United States Patent [19]

Kuboyama

[11] Patent Number: 5,219,758

[45] Date of Patent: Jun. 15, 1993

[54] HAIR GROWTH PROMOTING AGENT, PROCESS FOR PRODUCING AND APPARATUS

[76] Inventor: Nobuyoshi Kuboyama, 96 Litchfield Dr., Carlisle, Mass. 01741

[21] Appl. No.: 865,618

[22] Filed: Apr. 9, 1992

[51] Int. Cl.⁵ .......................... C12C 1/00; A01J 11/04
[52] U.S. Cl. ...................................... 435/302; 99/467
[58] Field of Search ................ 435/302; 99/467, 470

[56] References Cited

U.S. PATENT DOCUMENTS 4,776,104 10/1988 Kuoyama .......................... 34/77

Primary Examiner—John W. Rollins
Attorney, Agent, or Firm—Barry R. Lipsitz

[57] ABSTRACT

A hair growth promoting agent containing an effective ingredient extracted from malt is provided in accordance with the invention. It has also been discovered that malt is an effective hair growth promoting agent. A process for producing an extract of the effective ingredient and a device are also provided.

3 Claims, 3 Drawing Sheets

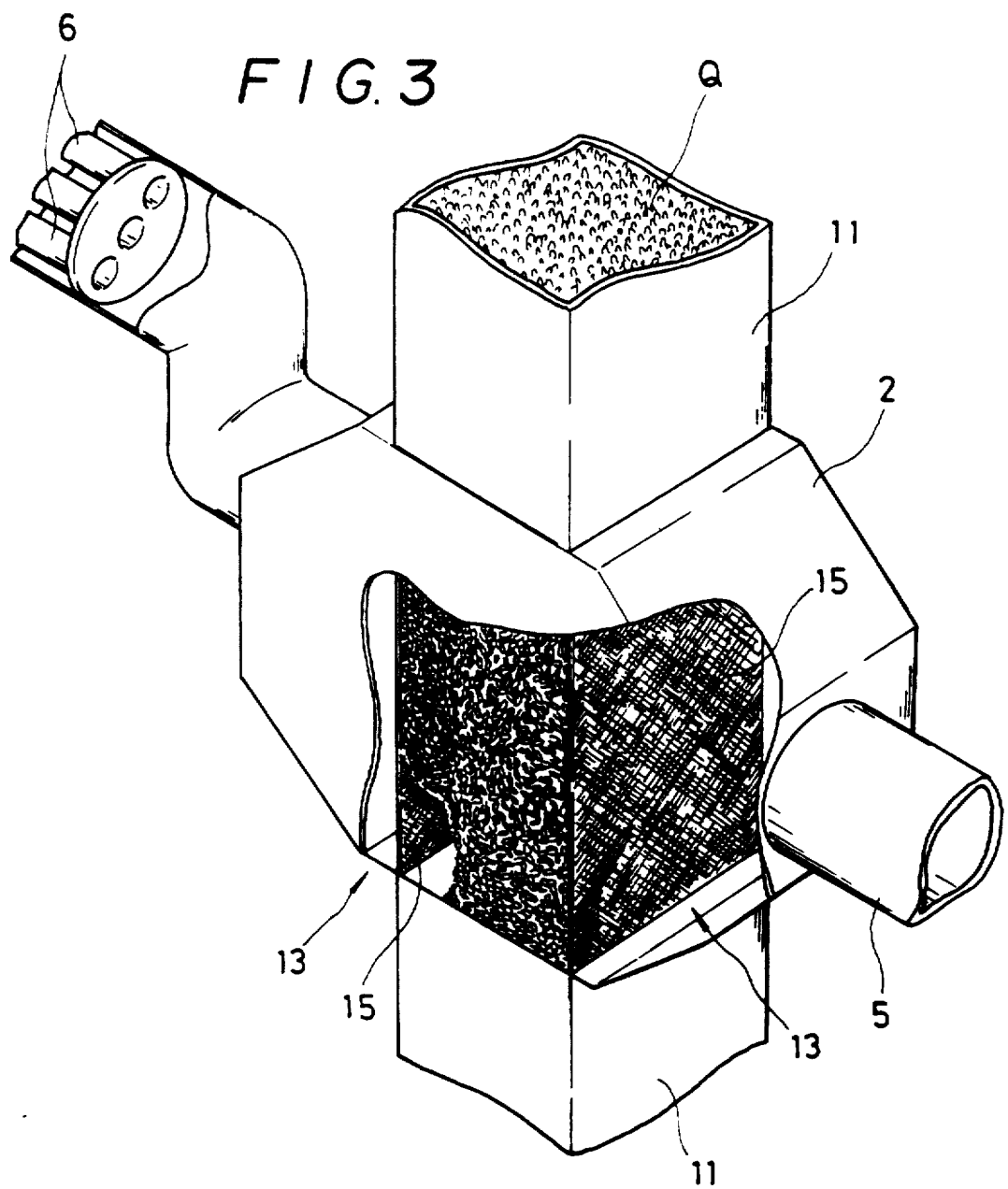
F I G. 3

HAIR GROWTH PROMOTING AGENT, PROCESS FOR PRODUCING AND APPARATUS

FIELD OF THE INVENTION

This invention relates generally to hair growth promoting agents, processes for producing hair growth promoting agents and extraction devices and, in particular, to a hair growth promoting agent that includes malt or an extract of an effective ingredient of malt, a process for producing the hair growth promoting agent from malt and an apparatus for producing the hair growth promoting agent.

BACKGROUND OF THE INVENTION

Malt is obtained by germinating barley, which includes a large amount of amylase. Malt is used in the manufacture of beer, millet honey and the like.

It has been thought that hairlessness and depilation are caused by factors such as activation of male sex hormones in organs such as the root of the hair, sebaceous glands and the like; a decrease in the quantity of blood flow to the hair follicles; excess secretion from the sebaceous glands; peroxide generation; fungi propagation; hereditary elements; nerve disease caused by stress; secondary disease; aging; and the like. Materials with ingredients that are effective for removing and reducing these causes have been used for the purpose of increasing hair growth and as hair cultivating agents.

However, preventing activation of male sex hormones and increasing the quantity of blood flow into hair follicles are not sufficient to prevent hairlessness and depilation. The mechanisms of depilation and hair growth are extremely complicated. Furthermore, it is nearly impossible to regenerate hair on a hairless spot once the hair has fallen off.

SUMMARY OF THE INVENTION

A hair growth promoting agent containing an effective ingredient obtained from malt is provided in accordance with the invention. In one embodiment, the effective ingredient of the malt is extracted using known extraction processes. In a second embodiment, the effective ingredient is extracted by a process including the steps of maintaining the malt in a decompression chamber at a first predetermined temperature; preparing a vapor, a mist or a mixture of a vapor and a mist from a liquid material; heating the vapor, mist or mixture of vapor and mist to a second predetermined temperature that is higher than the first predetermined temperature; introducing the heated vapor, mist or mixture into the decompression chamber so as to contact the malt contained therein and form a dew on the surface thereof; steeping the effective ingredient that is present on the surface of the malt in the dew; absorbing the effective ingredient into the dew and into the vapor, mist or mixture that did not form a dew while passing through the decompression chamber and revaporizing the dew including the effective ingredient in the decompression chamber; withdrawing the revaporized dew from the decompression chamber; and, cooling the withdrawn revaporized dew to yield an extract of the effective ingredient in a liquid state. An extraction apparatus for carrying out the process is also provided in accordance with the invention.

DETAILED DESCRIPTION OF THE PREFERRED EMBODIMENTS

The named inventor herein has unexpectedly discovered that malt acts to promote hair growth and is effective for increasing hair growth and decreasing depilation. The mechanism of action is unknown.

Extract of malt was accidentally applied to hairless skin and as a result the skin became soft and glossy. The inventor then washed the skin of his head with the extract several times in an effort to improve the skin and prevent dandruff. This skin became itchy at the spot of depilation and the inventor continued to apply the extract only to that spot. Initially, downy hair began to grow on the spot. Subsequent application of the extract caused the downy hair to change to normal hair.

In one embodiment of the invention, malt is used as an agent for promoting hair growth. The malt can be Pilsner Malt, Crystal Malt/Light, Mild Ale Malt, Vienna Malt, Klages Malt, Pale Malt, Lager Malt and the like as well as malt used in the manufacture of beer. In an alternate embodiment, an extract of an effective ingredient for promoting hair growth is obtained from malt by known methods using extraction solvents such as water, methanol, ethanol, acetone and the like.

In an alternate process, the extract of the effective ingredient is obtained by a process including the steps of maintaining the malt in a decompression chamber at a first predetermined temperature; preparing a vapor, a mist or a mixture of a vapor and a mist from a liquid material; heating the vapor, mist or mixture of vapor and mist to a second predetermined temperature that is higher than the first predetermined temperature introducing the heated vapor, mist or mixture into the decompression chamber so as to contact the malt contained therein and form a dew on the surface thereof; steeping the effective ingredient that is present on the surface of the malt in the dew; absorbing the effective ingredient into the dew and into the vapor, mist or mixture that did not form a dew while passing through the decompression chamber and revaporizing the dew including the effective ingredient in the decompression chamber; withdrawing the revaporized dew from the decompression chamber; and cooling the withdrawn revaporized dew to yield an extract of the effective ingredient in a liquid state. It is preferable to use extract obtained by this process because it is more effective for growing hair.

Figure 1:
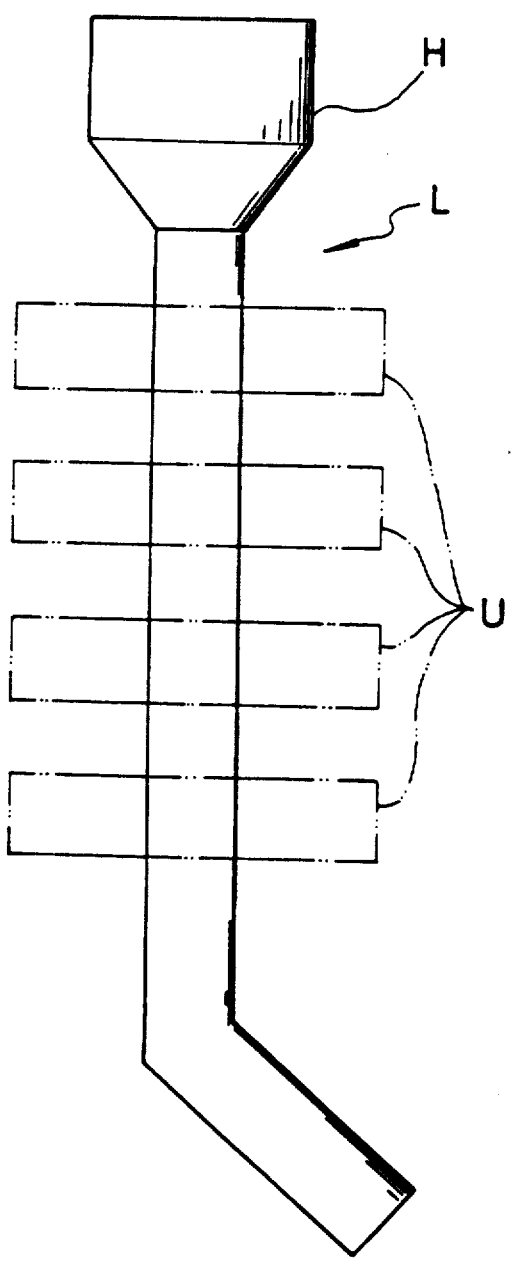
FIG. 1 is a diagram of an extraction device constructed and arranged in accordance with the invention.

A first embodiment of an extraction apparatus is shown in FIG. 1. The extraction apparatus includes multiple extract units U, a hopper H and a conveyance means L provided at a right angle to the extract units U. Malt contained in the hopper H is transferred in a vertical direction from the hopper H into the four extract units U by the conveyance means L. The effective ingredient is extracted in the extract units U.

Figure 2:
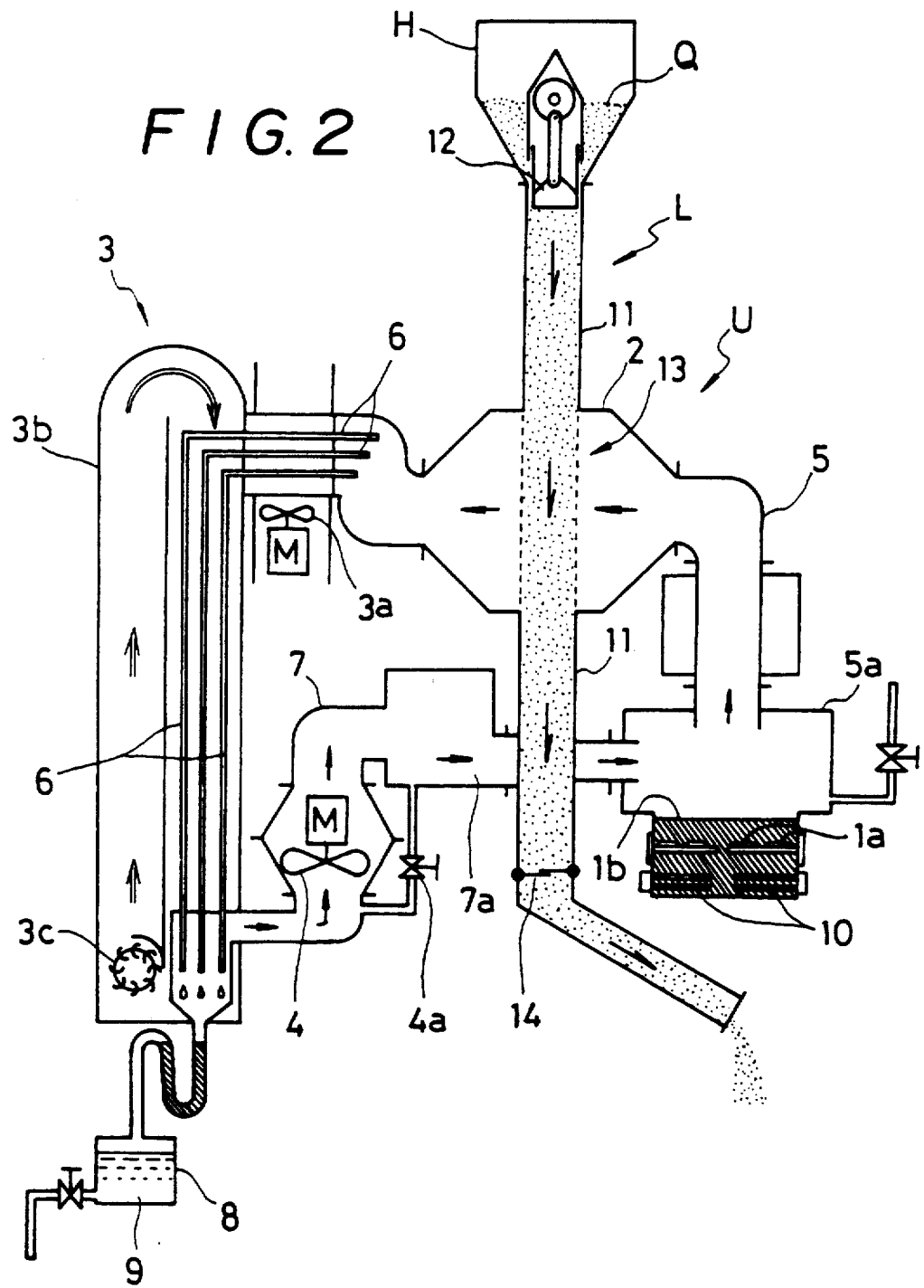
FIG. 2 is a diagram showing the relationship between the extraction units and a conveyance means in the device of FIG. 1; and, FIG. 3 is a diagram representing the relationship between a decompression chamber and a conveyance duct in the device of FIGS. 1 and 2.

FIG. 2 shows the construction of an individual extract unit U. The extract unit U includes an atomization chamber 1 for preparing a vapor, a mist or a mixture of a vapor and a mist from a liquid material 1b, a decompression chamber 2, a cooling means 3 and a high-pressure multistage blower 4, which functions as a decompression means. A first circulatory pipe 5 connects the atomization chamber 1 and the decompression chamber 2. A vapor, a mist or a mixture of a vapor and a mist passes through the first circulatory pipe 5 and is heated to a first predetermined temperature by a first heating means 5a. The decompression chamber 2 is connected to a decompression means 4 by a second circulatory pipe 6. The second circulatory pipe 6 includes multiple thin pipes for keeping materials cool. A third circulatory pipe 7 connects the decompression means 4 and the atomization chamber 1 and includes a second heating means 7a.

A tank 8 is used for storage of an extract 9 obtained from malt. An oscillating element 1a of an ultrasonic oscillator is provided in the liquid material 1b within the atomization chamber 1. A heater 10 is used for heating the liquid material 1b. The cooling means 3 includes a cooling chamber 3b having an airblast fan 3a and a cooling device 3c. A decompression controlling valve 4a delicately controls the reduced pressure value.

A conveyance means L includes a conveyance duct 11 provided at a right angle to the extract units U, a pressure means 12 for transferring malt downward, a ventilation portion 13 and a pressure controlling means 14. The conveyance duct 11 penetrates the decompression chamber 2 of the extract units U. The vapor, mist or mixture of vapor and mist is transferred through the ventilation portion 13 of the conveyance duct 11 in the decompression chamber 2. The pressure means 12 provided at the top of the conveyance duct 11 includes a piston driven by a motor. The pressure controlling means 14 provided at the bottom of the conveyance duct 11 includes a pressure dispersing board and a pressure dumper for controlling the speed of the falling malt inside the conveyance duct 11. The conveyance duct 11 includes multiple vibration motors for preventing the malt from sticking to the inside of the convayance duct 11.

In order to extract an effective ingredient from malt using the apparatus provided in accordance with the invention, a liquid material 1b is introduced into the atomization chamber 1 and malt is introduced into the decompression chamber 2. The liquid material 1b is heated by the heater 10 and forms a vapor, a mist or a mixture of a vapor and a mist as a result of the action of the oscillating element 1a. The quantity of the vapor, mist or mixture of vapor and mist that is generated is controlled by the number of oscillating elements, the heating temperature and the like. The pressure in the decompression chamber 2 is reduced by the action of the high pressure blower 4 and the vapor, mist or mixture thereof is drawn from the atomization chamber 1 into the decompression chamber 2 through the first circulatory pipe 5. The vapor, mist or mixture is further heated by the heater 5a by the first heating means 1 in the circulatory pipe 5 to a temperature higher than the temperature of the material in the decompression chamber 2. The vapor, mist, or mixture of vapor and mist entering the decompression chamber 2 contacts the malt at the lower temperature and forms a dew on the surface of the malt material. The portion of the vapor, mist or mixture that fails to contact the material or form a dew on the surface of the material passes through the chamber 2. At the same time, the effective ingredient of the malt is steeped in the dew on the surface of the material due to the action of the reduced pressure within the decompression chamber 2. Accordingly, the dew absorbs the effective ingredient and is revaporized due to the reduced pressure.

The revaporized dew including the effective ingredient and the remaining vapor, mist or mixture is withdrawn into the cooling means 3 through the second circulatory pipe 2 by the action of vaporization. The vapor, mist or mixture is cooled quickly, liquified within the second circulatory pipe 2 by the cooling means 3 and dripped into the tank 8 for storage. The extract 9 containing the effective ingredient of the malt is stored in the tank 8. The vapor, mist or mixture that is not liquified is heated by the heater 7*a* as the second heating means and is reintroduced into the atomization chamber 1 as a result of the action of the high pressure blower 4 through the third circulatory pipe 7.

FIG. 3 shows the relationship between the conveyance duct 11 and the decompression chamber 2. The ventilation portion 13 is provided on the side of the conveyance duct 11 that penetrates the decompression chamber 2. A net 15 and another net 15 are provided along portions of the holes for adjusting the amount of ventilation and thereby the quantity of the vapor, mist or mixture that passes through. The effective ingredient is extracted from the malt while the malt Q is transferred onto the net. The nets are manually or automatically controlled to change the quantity of the vapor, mist or mixture.

Reference is made to FIGS. 1 and 2 to illustrate the operation of the extraction device provided in accordance with the invention. When the device is switched on, the pressure means 12 begins to operate, the malt in the hopper H is provided in the conveyance duct 11 and falls downward at a predetermined speed. At the same time, the four extract units begin to operate in the manner described in connection with FIG. 2. The pressure in the decompression chamber is reduced by the action of the high pressure blower 4 and the vapor, mist or mixture thereof is withdrawn into the decompression chamber 2.

The vapor, mist or mixture that is present forms a dew on the surface of the malt that is being transferred at a predetermined speed between the first net 15 and the second net 15 that is within the ventilation portion 13. At the same time, the effective ingredient of the malt is present on the surface of the malt due to the redueced pressure acting on the malt and the vapor, mist or mixture forms a dew on the surface. The effective ingredient is absorbed into the dew and the dew is revaporized. The revaporized dew containing the effective ingredient passes through the pipes 6 as the second circulatory pipes provided within the upper area of the decompression chamber 3 and is cooled by the cooling means 3, liquified and stored in the tank 8. The vapor, mist or mixture that is not liquified is heated by the heater 7*a* and is reintroduced into the atomization chamber 1 as a result of the action of the high pressure blower 4. Accordingly, the effective ingredient is extracted from the malt within the four decompression chambers 2 while the malt is transferred downward inside the conveyance duct 11.

It takes about seven minutes for the malt to enter and leave the decompression chamber 2. It is also necessary to maintain the temperature of the vapor, mist or mixture entering the decompression chamber 2 at a temperature higher than the temperature of the malt, preferably between about 35° and 65° C., during this period.

The extract 9 obtained by this process can be used as is or it can be diluted prior to use. The extract is effective as a hair growth promoting agent.

The following experiments were carried out. It is understood that these experiments are presented for illustration purposes only and are not to be construed in a limiting sense.

Experiments 1-15

Fifteen male subjects were divided into three groups A, B and C so that each group had five subjects. All of the subjects had hairless spots of about 7 cm in diameter on their heads. Their average age was 50 years old.

The subjects in group A were given laboratory liquid a, the subjects in group B were given laboratory liquid b and the subjects in group C were give laboratory liquid c in order to compare the effects of laboratory liquids a, b and c.

Laboratory liquid a was prepared using 1000 g of malt. The malt was broken into pieces of less than 20 μm in diameter. The broken grains were stirred with 4000 cc of water to form a paste.

Laboratory liquid b was prepared by soaking 1000 g of malt in 4000 cc of ethanol for 12 hours and filtering the ethanol.

Laboratory liquid c was prepared by extracting 1000 g of malt by the following process: The malt was maintained in a decompression chamber at a first predetermined temperature. The pressure in the decompression chamber was maintained at 130 mmAg. A vapor, mist or mixture of a vapor and a mist was prepared from a liquid material and heated to a second predetermined temperature of between about 35° and 65° C., which was higher than the first predetermined temperature. The heated vapor, mist or mixture was introduced into the decompression chamber so as to contact the malt in the decompression chamber and form a dew on the surface of the malt. The effective ingredient was present on the surface of the malt and was steeped in the dew for a period of seven minutes. This caused the effective ingredient to be absorbed into the dew and into the vapor, mist or mixture that did not form a dew while passing through the decompression chamber. The dew containing the effective ingredient was revaporized in the decompression chamber and the revaporized dew was withdrawn from the decompression chamber. The withdrawn revaporized dew was cooled to yield 300 cc of an extract of the effective ingredient in a liquid state. This process was carried out four times so that the total extraction period was 28 minutes and the total quantity of extract was 1200 cc. The apparatus used to carry out this process is shown in FIGS. 1 to 3 in accordance with the present invention.

Each subject applied between about three and seven cc of laboratory liquid to their heads or to the center hairless spots of their heads twice a day, in the morning and in the evening. The spots to which the laboratory liquid was applied was hand massaged after application of the laboratory liquid.

The results of the experiment were:
Day 1 to Day 3
 Group A - No change observed.
 Group B - No change observed.
 Group C - Depilation began to stop.
Day 4 to Day 5
 Group A - No change observed.
 Group B - No change observed.
 Group C - The hairless spot became a sunburnt color. An itchy sensation began.
Day 10 to Day 14
 Group A - No change observed.
 Group B - No change observed.
 Group C - Pores began to appear on the hairless spot. Downy hair began to grow around the hairless spot.
Week 3
 GroupA - The amount of depilation was reduced.
 GroupB - The amount of depilation was reduced.
 Group C - Downy hair grew prosperously on the hairless spot. The downy hair which had previously grown around the hairless spot began to change to normal hair. The diameter of the hairless spot was reduced to about 3 cm.
Week 5
 GroupA - Downy hair began to appear on the hairless spot.
 GroupB - Downy hair began to appear on the hairless spot.
 Group C - Growth of downy hair on the hairless spot and transformation of the downy hair to normal hair was prosperous. The hairless spot was thinly covered with hair.
Month 2
 GroupA - The downy hair continued to grow, but little of the downy hair changed to normal hair.
 GroupB - The downy hair continued to grow, but little of the downy hair changed to normal hair.
 GroupC - Hair growth proceeded well. The hairless spot became inconspicuous.

As demonstrated, laboratory liquids a and b containing malt had an effect of causing hair to grow on a hairless area. Laboratory liquid c containing an extract of malt soybeans had a more significant effect in promoting hair growth. Accordingly, an effective hair growth promoting agent containing an effective ingredient extracted from malt is provided in accordance with the invention.

What is claimed is:

1. A device for extracting an effective ingredient for promoting hair growth from malt comprising:
 a supply tank for malt;
 at least two extract units for extracting the effective ingredient from the malt;
 a conveyance means for conveying the malt from the supply tank to the extract units;
 wherein each extract unit includes an atomization chamber in which a liquid material can be atomized, a decompression chamber connected to the atomization chamber by a first circulatory pipe in which the malt is maintained at a reduced pressure, a decompression means connected to the decompression chamber by a second circulatory pipe, a third circulatory pipe connecting the atomization chamber to the decompression chamber, a first heating means provided within the first circulatory pipe, a cooling means provided within the second circulatory pipe, and a second heating means provided within the third circulatory pipe; and,
 wherein the conveyance means includes a conveyance duct penetrating the decompression chamber at a right angle to the chamber, a pressure means provided at the top of the conveyance pipe by which malt is transferred inside the conveyance duct, and a pressure controlling means provided at the bottom of the conveyance duct.

2. The device of claim 1 wherein the cooling means includes a first cooling means and a second cooling means.

3. The device of claim 1 wherein the decompression means includes a circulatory fan.

* * * * *

UNITED STATES PATENT AND TRADEMARK OFFICE
CERTIFICATE OF CORRECTION

PATENT NO. : 5,219,758

DATED : June 15, 1993

INVENTOR(S) : Nobuyoshi Kuboyama

It is certified that error appears in the above-identified patent and that said Letters Patent is hereby corrected as shown below:

Column 6, line 52 (Claim 1 line 16) delete "chamber" (second occurrence) substitute therefor --means--

Signed and Sealed this

Twelfth Day of March, 1996

Attest:

BRUCE LEHMAN

Attesting Officer  Commissioner of Patents and Trademarks